United States Patent [19]

Alt et al.

[11] Patent Number: 5,399,636
[45] Date of Patent: Mar. 21, 1995

[54] METALLOCENES AND PROCESSES THEREFOR AND THEREWITH

[75] Inventors: Helmut G. Alt; Konstantinos Patsidis, both of Bayreuth, Germany; M. Bruce Welch; Rolf L. Geerts, both of Bartlesville, Okla.; Bernd Peifer, Bayreuth, Germany; Syriac J. Palackal, Bartlesville, Okla.

[73] Assignee: Phillips Petroleum Company, Bartlesville, Okla.

[21] Appl. No.: 75,712

[22] Filed: Jun. 11, 1993

[51] Int. Cl.⁶ .............................. C08F 4/648
[52] U.S. Cl. ................... 526/129; 526/130; 526/156; 526/160; 526/170; 502/104; 502/117; 502/120; 502/152; 502/153
[58] Field of Search .............. 526/129, 130, 156, 170, 526/160; 502/104, 117, 120, 152, 153

[56] References Cited

U.S. PATENT DOCUMENTS

| | | | |
|---|---|---|---|
| 3,426,069 | 2/1969 | Fritz et al. | 260/562 |
| 4,015,059 | 3/1977 | Karol | 526/130 |
| 4,530,912 | 7/1985 | Pullukat et al. | 502/104 |
| 4,530,914 | 7/1985 | Ewen et al. | 502/113 |
| 4,702,432 | 10/1987 | Welborn | 502/113 |
| 4,808,561 | 2/1989 | Welborn | 502/104 |
| 4,892,851 | 1/1990 | Ewen et al. | 502/104 |
| 5,086,025 | 2/1992 | Chang | 502/117 |
| 5,132,381 | 7/1992 | Winter et al. | 526/160 |
| 5,202,398 | 4/1993 | Antberg et al. | 526/129 |
| 5,210,352 | 5/1993 | Alt et al. | 585/375 |
| 5,243,001 | 9/1993 | Winter et al. | 526/127 |
| 5,276,208 | 1/1994 | Winter et al. | 556/53 |

FOREIGN PATENT DOCUMENTS

| | | |
|---|---|---|
| 0293815 | 7/1988 | European Pat. Off. . |
| 387690 | 9/1990 | European Pat. Off. . |
| 0420436 | 3/1994 | European Pat. Off. . |

OTHER PUBLICATIONS

Chem. Abstr. 112:159190q (1990).
Chem. Abstr. 112:236036y (1990).
Chem. Abstr. 121:36454.

*Primary Examiner*—Mark Nagumo
*Attorney, Agent, or Firm*—Lucas K. Shay

[57] ABSTRACT

A composition is provided comprising a metallocene having the formula of:

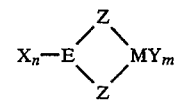

wherein each Z can be the same or different hydrocarbyl radical selected from the group consisting of cyclopentadienyl, indenyl, tetrahydroindenyl, fluorenyl, and mixtures thereof; each X can be the same or different and is selected from the group consisting of hydrogen, fluorine, chlorine, bromine, iodine, R, OR, $NR_2$, $PR_2$, or OQ, or mixtures thereof wherein the R is a $C_1$–$C_{20}$ hydrocarbyl radical and Q is an inorganic moiety selected from the group consisting of silica, alumina, clay, phosphated alumina, and mixtures thereof; each Y can be the same or different and is an alkyl group, hydrogen, fluorine, chlorine, bromine, iodine, or mixtures thereof; E is selected from C, Sn, Si, Ge, B, Al, N, or P; M is a metal selected from Ti, Zr, Hf, Sc, Y, V, or La; m is a number sufficient to fill out the valences of metal M; and n is 1 or 2. Also provided is a process for preparing the metallocene by contacting a hydrocarbon having an acidic, replaceable hydrogen with an organolithium and an organohalosilane to prepare a ligand which is then contacted with an organo alkali metal compound to form a bridged ligand followed by contacting the bridged ligand with an organolithium and a metal halide. The composition is useful for olefin polymerization, hydrogenation, alkene epoxidation, alkene isomerization, and ketone reduction.

54 Claims, No Drawings

METALLOCENES AND PROCESSES THEREFOR AND THEREWITH

FIELD OF THE INVENTION

The present invention relates to a metallocene composition, a process for preparing the composition, and a process for using the composition.

BACKGROUND OF THE INVENTION

Since the discovery of ferrocene in 1951, a number of metallocenes have been prepared by tile combination of anions having the cyclopentadienyl structure with various transition metals. The term "cyclopentadienyl structure" as used herein refers to the following structure.

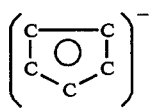

Such "cyclopentadienyl structure" can be formed by addition of various metal alkyls to cyclopentadiene and "cyclopentadiene-type" compounds.

The term "cyclopentadiene-type compound" as used herein refers to compounds containing the cyclopentadienyl structure. Examples of cyclopentadiene-type compounds include unsubstituted cyclopentadiene, unsubstituted indene, unsubstituted tetrahydroindene, unsubstituted fluorene, and substituted varieties of such compounds.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and substitutions on cyclopentadienyl-type ligands has been found to affect the activity of the catalyst, the stereoselectivity of the catalyst, the stability of the catalyst, and other properties of the resulting polymer; however, the effects of various substituents is still largely an empirical matter, that is, experiments must be conducted in order to determine just what effect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

While there are references in the prior art which have envisioned metallocenes, there is no known reference disclosing bridged metallocenes chemically bonded to an inorganic support which can be used in a heterogeneous system such as, for example, heterogeneous catalyst for olefin polymerization. It would be a contribution to the art if a bridged metallocene or ligand chemically bonded to an inorganic support is provided. It would also be a contribution to the art if a process for making or using the bridged metallocene or ligand chemically bonded to an inorganic support is developed.

SUMMARY OF THE INVENTION

An object of the present invention is to provide certain new bridged ligands and metallocenes. Another object of the present invention is to provide a method for preparing new bridged ligands and metallocenes. A further object of the present invention is to provide supported, bridged ligands and metallocenes. Yet a further object of the present invention is to provide a process for preparing the supported, bridged ligands and metallocenes. Still another object of the present invention is to provide polymerization catalysts employing the supported, bridged metallocenes. Yet another object of the present invention is to provide processes for the polymerization of olefins using the supported, bridged metallocene catalyst systems. Still yet another object of the present invention is to provide polymers produced using such supported, bridged metallocene catalysts.

According to a first embodiment of the invention, a composition is provided which comprises a bridged metallocene having the formula of

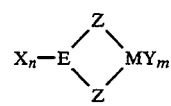

wherein each Z can be the same or different, substituted or unsubstituted, hydrocarbyl radical selected from the group consisting of cyclopentadienyl, indenyl, tetrahydroindenyl, fluorenyl, and mixtures thereof; each X can be the same or different and is selected from the group consisting of hydrogen, fluorine, chlorine, bromine, iodine, R, OR, NR$_2$, PR$_2$, or OQ, or mixtures thereof wherein the R is a C$_1$-C$_{20}$ hydrocarbyl radical and Q is an inorganic moiety selected from the group consisting of silica, alumina, clay, phosphated alumina, and mixtures thereof; each Y can be the same or different and is an alkyl group, hydrogen, fluorine, chlorine, bromine, iodine, or mixtures thereof; E is selected from C, Sn, Si, Ge, B, Al, N, or P; M is a metal selected from Ti, Zr, Hf, Sc, Y, V, or La; m is a number sufficient to fill out the remaining valences of the metal M; n is an integer of 1 or 2; and the C$_1$-C$_{20}$ hydrocarbyl radical can be an alkyl, alkenyl, aryl, cycloalkyl, aralkyl, alkaryl, or mixtures thereof.

According to a second embodiment of the invention, a process is provided which comprises contacting a bridged ligand having the formula of ZH-EX$_n$-ZH with an inorganic material QOH to form a bridged ligand which is chemically bonded to the inorganic moiety Q, wherein each Z can be the same or different, substituted or unsubstituted, hydrocarbyl radical selected from the group consisting of cyclopentadienyl, indenyl, tetrahydroindenyl, fluorenyl, and mixtures thereof; each X can be the same or different and is selected from the group consisting of hydrogen, fluorine, chlorine, bromine, iodine, R, OR, NR$_2$, PR$_2$, OQ, and mixtures thereof wherein the R is a C$_1$-C$_{20}$ hydrocarbyl radical and Q is an inorganic moiety selected from the group consisting of silica, alumina, clay, phosphated alumina, and mixtures thereof, but one X must be a halogen; E is selected from C, Sn, Si, Ge, B, Al, N, or P; n is an integer of 1 or 2; preferably at least one X is a halogen; and the C$_1$-C$_{20}$ hydrocarbyl radical can be an alkyl, alkenyl, aryl, cycloalkyl, aralkyl, alkaryl, or mixtures thereof.

According to a third embodiment of the invention, a process for preparing a bridged metallocene having the formula of

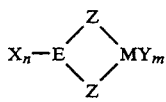

is provided which comprises: (1) contacting a hydrocarbon having at least two acidic, replaceable hydrogens and having the formula of $ZH_2$ with an organolithium and an organohalocompound to prepare a ligand precursor having the formula of $HZ\text{-}EX_{n+1}$ wherein at least two X are preferably halogens and n is an integer of 1 or 2; (2) contacting the ligand precursor with an organo alkali metal compound having the formula of HZMa to form a bridged ligand having the formula of $ZH\text{-}EX_n\text{-}ZH$ wherein n is an integer of 1 or 2 and preferably at least one X is a halogen; (3) contacting the bridged ligand with an inorganic material QOH to form a bridged ligand chemically bonded to the inorganic moiety Q; (4) contacting the bridged ligand chemically bonded to Q with an organolithium and a metal halide having the formula of $MY_m$ to prepare the bridged metallocene; wherein each Z can be the same or different, substituted or unsubstituted, hydrocarbyl radical selected from the group consisting of cyclopentadienyl, indenyl, tetrahydroindenyl, fluorenyl, and mixtures thereof; each X can be the same or different and is selected from the group consisting of hydrogen, fluorine, chlorine, bromine, iodine, R, OR, $NR_2$, $PR_2$, or OQ, or mixtures thereof wherein the R is a $C_1\text{-}C_{20}$ hydrocarbyl radical and Q is an inorganic moiety selected from the group consisting of silica, alumina, clay, phosphated alumina, and mixtures thereof; each Y can be the same or different and is an alkyl group, hydrogen, fluorine, chlorine, bromine, iodine, or mixtures thereof; each E is selected from C, Sn, Si, Ge, B, Al, N, or P; M is a metal selected from Ti, Zr, Hf, Sc, Y, V, or La; m is a number sufficient to fill out the remaining valences of metal M; Ma is an alkali metal; n is an integer of 1 or 2; and the $C_1\text{-}C_{20}$ hydrocarbyl radical is an alkyl, alkenyl, aryl, cycloalkyl, aralkyl, alkaryl, or mixtures thereof.

According to a fourth embodiment of the invention, a process for olefin polymerization is provided which comprises contacting an olefin under olefin polymerization conditions with a composition comprising a bridged metallocene as described above, optionally, in combination with a suitable activator selected from the group consisting of organoaluminum compounds, organoaluminoxanes, tris-perfluorophenyl borate, trityl tetra-perfluorophenyl borate, and mixtures thereof.

Accordingly to a fifth embodiment of the invention there is provided a polymer product resulting from the polymerization process of the fourth embodiment of the invention.

DETAILED DESCRIPTION OF THE INVENTION

According to the first embodiment of the invention, a composition useful as a catalyst for olefin polymerization comprises a bridged metallocene having the formula of

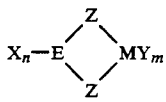

The term "metallocene" used herein refers to an organometallic compound containing two "cyclopentadienyl structures" unless otherwise indicated. The term "bridged" used herein refers to, unless indicated otherwise, two cyclopentadienyl structures bonded together through a "bridging" element E. Each Z in the formula can be the same or different hydrocarbyl radical selected from the group consisting of cyclopentadienyl, indenyl, tetrahydroindenyl, fluorenyl, and mixtures thereof. These hydrocarbyl radicals can be unsubstituted or substituted. The substituents can be other hydrocarbyl radicals which include, but are not limited to, $C_1\text{-}C_{10}$ alkyl groups, $C_6\text{-}C_{12}$ aryl groups, $C_1\text{-}C_{10}$ cycloalkyl groups, $C_1\text{-}C_{10}$ alkenyl groups, or mixtures thereof. The substituents can also be halogens, amines, hydroxyls, heteroatoms such as for example N, P, Si, O and Sn, and mixtures thereof. The presently preferred Z is a fluorenyl radical, a cyclopentadienyl radical, or mixtures thereof.

The E in the formula is an element selected from the group consisting of Sn, C, Si, Ge, B, Al, N, P, and mixtures thereof. The presently preferred element is Si.

The M in the formula is a metal selected from the group consisting of Ti, Zr, Hf, Sc, Y, V, and La. The presently preferred metal is Ti, Zr, V, or Hf. Each Y in the formula can be the same or different and is selected from the group consisting of an alkyl group having 1 to about 20 carbon atoms, hydrogen, fluorine, chlorine, bromine, iodine, and mixtures thereof. The presently preferred Y is chlorine or methyl group.

Each X in the formula can be the same or different and is selected from the group consisting of hydrogen, fluorine, chlorine, bromine, iodine, R, OR, $NR_2$, $PR_2$, OQ, and mixtures thereof wherein the R is a $C_1\text{-}C_{20}$ hydrocarbyl radical selected from the group consisting of alkyl, alkenyl, aryl, aralky, alkaryl, and mixtures thereof and Q is an inorganic moiety selected from the group consisting of silica, alumina, phosphated alumina, clay, and mixtures thereof. The presently preferred X is chlorine, a short chain alkyl group such as for example methyl group, an OQ such as for example -O-silica, -O-alumina, or mixtures thereof. The presently most preferred is that at least one X be an OQ such as -O-silica, or -O-alumina, or mixtures thereof.

The phosphated alumina useful for the present invention can be prepared by the steps comprising: (1) mixing aluminum nitrate with a phosphate compound, in the presence of water, to form a solution; (2) adding a basic compound, preferably in aqueous form, to the solution to produce a solid product; (3) recovering the solid product; (4) optionally, washing the solid product with a solvent to prepare a washed-product; (5) drying the solid product or washed product, resulting in a dried product; and (6) calcining the dried product to produce the phosphated alumina. Suitable phosphate compounds include, but are not limited to ammonium phosphate (dibasic), ammonium phosphate (monobasic), sodium phosphate (monobasic), sodium phosphate (dibasic), magnesium phosphate, potassium phosphate (dibasic), potassium phosphate (monobasic), manganese phosphate, and mixtures thereof. The presently preferred phosphate compound is ammonium phosphate (monobasic) because of its ready availability and easy of use. Suitable basic compound employed in step (2) should be able to produce a precipitate from the solution. Examples of suitable basic compound include, but are not limited to, ammonium hydroxide, lithium hydroxide, sodium hydroxide, sodium carbonate, sodium bicarbonate, potassium hydroxide, magnesium hydroxide, barium phenoxide, calcium hydroxide, calcium phenoxide, RONa, RSNa, and mixtures thereof wherein R is a $C_1$–$C_6$ alkyl radial. The presently preferred basic compound is ammonium hydroxide. The solvent used in step (4) to wash the solid product can be an alcohol, ether, ketone, acid, amide, or water, as long as it does not react with or solubilize the solid product. Examples of suitable solvent include, but are not limited to water, methanol, ethanol, propanol, isopropanol, butanol, isobutanol, pentanol, diethyl ether, tetrahydrofuran, acetone, methyl ethyl ketone, acetic acid, dimethylformamide, and mixtures thereof. The presently preferred solvents are water and ethanol because of their ready availability. The drying of step (5) can be a conventional drying or drying under reduced pressure. The drying temperature can vary widely from about 50° C. to about 150° C. under about 0.05 mmHg to about 800 mmHg pressure for about 1 to about 30 hours, preferably from 60° C. to 100° C. under 0.05 to 760 mmHg pressure for 5 to 20 hours. The calcining step can also vary widely from about 250° C. to about 1500° C., preferably 500° C. to 1000° C., under atmospheric pressure for about 30 minutes to about 15 hours, preferably 1 to 7 hours.

In the preparation of the phosphated alumina, the molar ratio of the phosphate compound to aluminum nitrate is generally in the range of from about 0.05:1 to about 5:1, preferably from about 0.1:1 to about 2:1, and most preferably from 0.2:1 to 1:1 for best physical form and catalytic activity of phosphated alumina when used as a component of the invention composition. The molar ratio of water to aluminum nitrate is in the range of from about 10:1 to about 200:1, depending on the solubility of both aluminum and the phosphate compound, preferably about 20:1 to about 100:1, most preferably 25:1 to 50:1. The molar ratio of the basic compound to aluminum nitrate is in the range of from about 0.05:1 to about 10:1, preferably about 0.2:1 to about 5:1 and most preferably 0.5:1 to 2:1. The recovery of the solid product in step (3) can be carried out by any known means such as, for example, filtration, decantation and centrifugation. The molar ratio of the washing solvent to aluminum nitrate can vary widely from about 5:1 to about 1000:1 depending on the type of solvent used. The washing can also be carried out more than once and/or with a different solvent.

The clay useful for the invention can be any kind of clay. Examples of suitable clays include, but are not limited to, kaolinite, halloysite, vermiculite, chlorite, attapulgite, smectite, montmorillonite, illite, saconite, sepiolite, palygorskite, Fuller's earth, and mixtures thereof. The presently preferred clay is a montmorillonite clay. The presently most preferred clay is sodium montmorillonite which is generally known as bentonire.

Illustrative, but non-limiting examples of bridged metallocenes include for example silica-O- 1-cyclopentadienyl- 1-cyclopentadienylmethylsilane zirconium dichloride, silica-O-bis(9-fluorenyl)phenylsilane zirconium dichloride, silica-O-1-cyclopentadienyl-9-fluorenylmethylsilane hafnium dichloride, silica-O-bis(9-fluorenyl)phenylsilane hafnium dichloride, silica-O- 1-cyclopentadienyl-9- fluorenylmethylsilane vandium dichloride, silica-O-bis(9-fluorenyl)phenylsilane vandium dichloride, silica-O- 1-cyclopentadienyl-9- fluorenylmethylsilane titanium dichloride, silica-O-bis(9-fluorenyl)phenylsilane titanium dichloride, silica-O-bis (2,8-difluoro-9- fluorenyl)methylsilane zirconium dichloride, silica-O-1-cyclopentadienyl-9- fluorenylmethylchlorosilane zirconium dichloride, silica-O-bis(9-fluorenyl)phenylchlorosilane zirconium dichloride, silica-O-1-cyclopentadienyl-9-fluorenylmethylchlorosilane hafnium dichloride, silica-O-bis(9-fluorenyl)phenylchlorosilane hafnium dichloride silica-O-cyclopentadienyl-9-fluorenylmethylchlorosilane vanadium dichloride, silica-O-bis (9-fluorenyl) phenylchlorosilane vandium dichloride, silica-O-1-cyclopentadienyl-9-fluorenylmethylchlorosilane titanium dichloride, silica-O-bis(9-fluorenyl)phenylchlorosilane titanium dichloride, silica-O-bis( 2,8-difluoro-9-fluorenyl )methylchlorosilane zirconium dichloride, silica-O-1-cyclopentadienyl-9-fluorenylmethylsilane zirconium dichloride, alumina-O-1-cyclopentadienyl-9-fluorenylmethylsilane zirconium dichloride, bentonire-0-1-cyclopentadienyl-9-fluorenylmethylsilane zirconium dichloride, and mixtures thereof. The presently preferred bridged metallocene is silica-O-1-cyclopentadienyl-9-fluorenylmethylsilane zirconium dichloride.

The composition of the first embodiment of the invention can be used in a variety of applications. For example;, the composition can be used as catalyst for hydrogenation, alkene epoxidation, alkene isomerization, ketone reduction, stereoselective alkene polymerization, and as reagent for stereoselective cobalt-mediated reactions, alkyltitanium addition reactions with aldehydes, and formation of allylic amines.

The bridged metallocenes disclosed in the first embodiment of the invention can be prepared by the process of the third embodiment of the invention disclosed herein below. The process of the second embodiment of the invention is detailed in the third step of the third embodiment of the invention. In the first step of the process of the third embodiment of the invention, a substituted or unsubstituted hydrocarbon having an acidic, replaceable hydrogen atom which has the formula of $ZH_2$ is contacted with an organolithium and an organohalocompound. Z is the same as that disclosed in the first embodiment of the invention. The presently preferred hydrocarbons having an acidic, replaceable hydrogen are pentadiene, cyclopentadiene, indene, tetrahydroindene, fluorene, or mixtures thereof. The preferred organolithium is an alkyllithium including butyllithium, methyllithium, ethyllithium, propyllithium, or mixtures thereof. The presently most preferred organolithium is butyllithium. The presently preferred organohalocompound is an alkylhalosilane or arylhalorosilane such as methyltrichlorosilane, ethyltrichlorosilane, propyltrichlorosilane, phenyltrichlorosilane, tolyltrichlorosilane, or mixtures thereof. The presently most preferred organohalocompound are methyltrichlorosilane, phenyltrichlorosilane, or mixtures thereof.

The first step of the third embodiment of the invention can also be carried out in the presence of a suitable solvent. Examples of suitable solvents include, but are not limited to diethyl ether, tetrahydrofuran, hydrocarbons such as pentane, hexane, heptane, cyclohexane, and toluene, amines such as N-vinyl-2-pyrrolidone tetramethylethylenediamine, pyridine and dimethylformamide, and mixtures thereof.

According to the present invention, the reaction pressure and temperature for the first step of the third embodiment are not particularly critical and can vary over a wide range. Atmospheric pressure is presently preferred although higher or lower pressures can be employed. Typically, the reaction temperature is in the range of from about −100° C. to about 100° C. Generally, it is convenient to carry out the first step at ambient temperatures.

The molar ratio of the hydrocarbon having at least two acidic, replaceable hydrogens to the organolithium can vary over a wide range depending on the results desired and is generally in the range of from about 5:1 to about 1:5, preferably about 2:1 to about 1:2, and most about 1:1. Similar molar ratios can be employed for the organohalocompound to the lithiated hydrocarbon. The molar ratio of the solvent, if employed, to the organolithium is generally in the range of from about 1000:1 to about 0.1:1, preferably about 500:1 to about 0.5:1.

In the second step of the third embodiment of the invention, the ligand formed during the first step has the formula of $ZH-EX_{n+1}$ wherein the scopes of E and X are the same as those disclosed in the first embodiment of the invention except that two X must be a halogen and n is an integer of 1 or 2. The ligand is then contacted with an organo alkali metal compound having the formula of HZMa wherein Z is the same as described above and Ma is an alkali metal. The presently preferred organo alkali metal compounds represented by the formula of HZMa include cyclopentadienylsodium, indenylsodium, tetrahydroindenylsodium, fluorenylsodium, cyclopentadienyllithium, indenyllithium, tetrahydroindenyllithium, fluorenyllithium, or mixtures thereof. The reaction conditions are the same as those disclosed in the first step of the third embodiment. The second step can also be carried out in the presence of a solvent. The scope of time solvent is the same as described above. The molar ratio of the ligand to the organo alkali metal compound can vary in a wide range and is generally in the range of from about 5:1 to about 1:5, preferably from about 2:1 to about 1:2, and most preferably about 1.2:1 to 1:1.2. The molar ratio of the solvent to the organo alkali metal compound is generally the same as that described for the solvent to the organolithium in the first step of this embodiment of the invention.

A bridged ligand having the formula of $ZH-EX_n-ZH$, wherein Z, E, X, and n are the same as those described in the first embodiment except that one X is preferably a halogen, is formed in the second step of the process. In the third step of the process, the bridged ligand thus formed is contacted with an inorganic material. The inorganic material is generally used as catalyst support and has the same scope as described above. Generally the contacting of the bridged ligand and the inorganic material can be carried out under the conditions described in the first step of the process. A solvent can also be present in the contacting of the bridged ligand and the inorganic material. The molar ratio of the bridged ligand to the inorganic material is generally dependent on the surface OH population of the inorganic material. It can range from about 1:1 to about 0.00001:1. The molar ratio of the solvent (if present) to the inorganic material can be the same as that of the solvent to the organolithium in the first step of the process. The contacting of the bridged ligand with the inorganic material under conditions described herein results in the formation of a bridged ligand which is chemically bonded to the inorganic material.

The bridged ligand chemically bonded to a inorganic support is further contacted with an organolithium and a metal halide having the formula of $MY_m$, in the fourth step of the process, under conditions to form a bridged metallocene. The scope of organolithium and metal halide is the same as that disclosed in the first step of the process. The definitions and scopes of M, Y, and m are the same as described above. The reaction conditions for this step are also the same as those described for the first step. Similarly, a solvent can also be present in the third step of the invention as in the first step. The scope of the solvent is the same as that in the first step and the molar ratio of the solvent to the organolithium in this step is the same as that of the solvent to the organolithium in the first step. The molar ratio of the bridged ligand to the organolithium can be in the range of from about 5:1 to about 1:5, preferably from about 3:1 to about 1:3, and most preferably about 1:2. The molar ratio of the organolithium to the metal halide is generally about 2:1 A bridged metallocene is formed in the fourth step of the process.

Alternatively, the contacting of the inorganic material can be carried out after a bridged metallocene is formed, i.e., the steps three and four are reversed. The conditions for the contacting are generally the same as those described immediately above.

The resulting bridged metallocene can be recovered and purified using conventional techniques known in the art such as filtration and extraction. It is generally desirable to recover the metallocene in a form that is free of any substantial amount of by-product impurities. As a general rule, it has been found that the metallocenes based on unbridged fluorenyl compounds are less stable than the metallocene compounds formed from bridged fluorenyl compounds. Since the stability of the various metallocenes varies, it is generally desirable to use the metallocenes soon after their preparation or at least to store the metallocene under conditions favoring their stability. For example the metallocenes can generally be stored in the dark, at low temperature, i.e. below 0° C., and in the absence of oxygen or water.

The bridged metallocenes can be used in combination with a suitable activator for the polymerization of olefinic monomers. In such processes the metallocene or the activator can be employed on a solid insoluble particulate support.

Examples of suitable activator include generally, organoaluminoxane, tris-perfluorophenyl borate, trityl tetra-perfluorophenyl borate, and any of those organometallic co-catalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, tri-isobutyl aluminum, diethyl aluminum chloride, diethyl aluminum hydride, and the like.

The currently most preferred activator is an organoaluminoxane. Such compounds include those compounds having repeating units of the formula

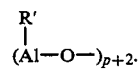

where R' is an alkyl group generally having 1 to 5 carbon atoms; and p is a number between 0 to about 100, preferably about 5 to about 50, and most preferably 10 to 40. The presently most preferred organoaluminoxane is methylaluminoxane. Organoaluminoxanes, also sometimes referred to as poly(hydrocarbyl aluminum oxides) are well known in the art and are generally prepared by reacting an organo hydrocarbylaluminum compound with water. Such preparation techniques are disclosed in U.S. Pat. No. 4,808,561, the disclosure of which is incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The bridged metallocenes in combination with the organoaluminoxane activator can be used to polymerize olefins. Such polymerizations would be carried out in a homogeneous system in which the catalyst and activator were soluble; generally, it is within the scope of the present invention to carry out the polymerizations in the presence of supported forms of the catalyst and/or activator in a slurry or gas phase polymerization. It is within the scope of the invention to use a mixture of two or more metallocenes or a mixture of an inventive bridged metallocene with one or more other types of metallocenes.

The bridged metallocenes when used with an organoaluminoxane are particularly useful for the polymerization of mono-unsaturated aliphatic alpha-olefins having 21 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. The catalysts are particularly useful for preparing copolymers of ethylene or propylene and generally a minor amount, i.e. no more than about 12 mole percent, more typically less than about 10 mole percent, of the higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

Generally the molar ratio of the aluminum in the organoaluminoxane to the transition metal in the metallocene would be in the range of about 0.1:1 to about $10^5$:1 and more preferably about 5:1 to about $10^4$:1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about $-60°$ C. to about $280°$ C., more preferably in the range of about $20°$ C. to about $160°$ C. Typically the pressure would be in the range of from about 1 to about 500 atmospheres or greater.

The polymers produced with this invention have a wide range of uses that will be apparent to those skilled in the art from the physical properties of the respective polymer. Some of the catalysts are useful for preparing syndiotactic polymers. The term syndiotactic polymer as used herein is intended to include those polymers having segments of more than 10 monomeric repeating units in which the alkyl group of each successive monomeric unit is on the opposite side of the plane of the polymer. Generally, the polymer segments having such syndiotactic microstructure are formed of at least about 40 monomeric repeating units in which the position of the alkyl group relative to the plane of the polymer alternates from one monomeric unit to the next monomeric unit.

EXAMPLES

A further understanding of the present invention, its various aspects, objects and advantages will be provided by the following examples. In these examples, all runs were routinely carried out using the Schlenk technique with the exclusion of oxygen and moisture. See generally, D. F. Shriver, The Manipulation of Air-sensitive Compounds, McGraw-Hill, 1969. Purified and dried argon served as protective gas. The solvent used were dried by distillation over a Na/K alloy (pentane, hexane, toluene, methylene chloride, ether and tetrahydrofuran) or phosphorus pentoxide under argon. Tetrahydrofuran was additionally purified over lithium alanate and methylene chloride was additionally purified over calcium hydride. Fluorene was purified over silica gel prior to use. Analogous procedures were followed by fluoranthene and phenanthrene. The propylene used for polymerization trials was purified for 1 hour at $30°$ C. using methylaluminoxane. A b.a.r. autoclave (1 liter) was used for the polymerization runs.

Example I

This example illustrates the preparation of an alkyl-fluorenylchlorosilane by reacting fluorene, a hydrocarbon having an acidic, replaceable hydrogen with an organolithium and an organochlorosilane.

The preparations were carried out by first slowly adding (dropwise) butyllithium (1.6M in hexane) to a solution of a hydrocarbon having an acidic, replaceable hydrogen (see Table I) in a solvent as noted in Table I. After the dropwise addition, the mixture was stirred for a period of a hour at $25°$ C. After removing the solvent, a solid organolithium was formed which was then added in portions to a solution of an organochlorosilane in a solvent followed by stirring for 1 hour at $25°$ C. The mixture resulting from the reaction was filtered over sodium sulfate in order to remove lithium chloride and the residue was washed twice with 150 mL, in each case, of pentane. The combined filtrates were concentrated by evaporation to 25% of the original volume and crystallized at $-30°$ C. A colorless crystalline product was obtained. The results are shown in Table I.

TABLE I

| Preparation of Alkylfluorenylchlorosilane | | | |
|---|---|---|---|
| Hydrocarbon | Butyl-lithium[a] | Organo-chlorosilane | Product[b] |
| fluorene (20 g; 120 mmol) | 75 ml | dimethyldichlorosilane (23.3 g; 180 mmol) in 700 ml pentane | 9-fluorenyl-dimethyl-chlorosilane (90%) |
| 2,7-di-t-butyl- | 11.2 ml | dimethyldi- | 9-(2,7-di-t- |

TABLE I-continued

Preparation of Alkylfluorenylchlorosilane

| Hydrocarbon | Butyl-lithium[a] | Organo-chlorosilane | Product[b] |
|---|---|---|---|
| fluorene (5 g; 18 mmol) | | chlorosilane (2.8 g) in 200 ml ether | butyl-fluorenyl)dimethyl-chlorosilane (85-90%) |
| 2,7-di-t-butyl-fluorene (5 g; 18 mmol) | 11.2 ml | diphenyldichlorosilane (2.8 g) in 200 ml ether | 9-(2,7-di-t-butyl-fluorenyl)diphenyl chlorosilane (85%) |

[a]Butyllithium used was 1.6 M solution in hexane.
[b]The value in parenthesis denotes product yield.

Example II

This example illustrates the synthesis of a bridged ligand in the preparation of the bridged metallocene of the invention by reacting the alkylfluorenylchlorosilane prepared in Example I with an organo alkali metal compound.

The runs were carried out by first dissolving an alkylfluorenylchlorosilane (quantity noted in Table II below) in a solvent shown in Table II followed by addition of an organo alkali metal compound as noted in Table II at 25° C. After being stirred for 4 hours at 25° C., the reaction mixture was hydrolyzed with 100 ml of saturated ammonium chloride solution resulting in phase separation. The organic phase was washed twice with water (100 ml each) followed by drying over sodium sulfate. A yellowish organic solution was concentrated by evaporation followed by recrystallization at −30° C. to obtain a powdery product. The results are shown in Table II.

TABLE II

Preparation of Silicon-Containing Ligands

| Alkylfluoroenyl-chlorosilane | Organo alkali Metal Compound | Solvent | Product[a] |
|---|---|---|---|
| 9-fluorenyldimethyl-chlorosilane (5 g; 20 m mole) | cyclopentadienyl sodium (3.4 g; 40 mmol) | ether (150 ml) | 1-cyclopentadienyl-9-fluorenyldimethylsilane (87%) |
| 9-fluorenyldimethyl chlorosilane (5 g; 20 mmol) | cyclopentadienyl sodium (3.4 g; 40 mmol) | tetrahydro-furon (150 ml) | 1-cyclopentadienyl-9-fluorenyldimethylsilane (87%) |
| 9-(2,7-di-t-butylfluor-enyl)dimethylchlorosilane (5 g; 13.5 m mole) | cyclopentadienyl sodium (3.4 g; 40 mmol) | ether (150 ml) | 1-cyclopentadienyl-9-(2,7-di-t-butylfluorenyl) dimethylsilane (88%) |
| 9-(2,7-di-t-butylfluor-enyl)diphenylchlorosilane (5 g; 13.5 m mole) | cyclopentedienyl sodium (3.4 g; 40 mmol) | ether (150 ml) | 1-cyclopentadienyl-9-(2,7-di-t-butylfluorenyl) diphenylsilane (82%) |
| 9-(2,7-di-t-butylfluor-enyl)dimethylchlorosilane (5 g; 13.5 m mole) | fluorenyllithium[b] (3.4 g) | ether (100 ml) + TMEDA (10 ml)[c] | 9-(2,7-di-t-butylfluor-enyl)-9'-fluorenyl-dimethylsilane (85%) |
| 9-(2,7-di-t-butylfluor-enyl)diphenylchlorosilane (5 g; 13.5 m mole) | fluorenyllithium[b] (3.4 g) | other (100 ml) + TMEDA (10 ml)[c] | 9-(2,7-di-t-butylfluor-enyl)-9'-fluorenyl-diphenylsilane (81%) |

[a]The value in parenthesis denotes product yield.
[b]Fluorenyllithium was prepared by dissolving 3.4 g of fluorene in 100 ml of ether followed by addition of 13 ml of butyllithium (1.6 M in hexane). After stirring for 4 hours at 25° C., the solvent was removed and the yellow product, fluorenyllithium, was dried under vacuum.
[c]TMEDA is an abbreviation for tetramethylethylenediamine.

Example III

This example illustrates the synthesis of a bridged metallocene by reacting the bridged ligand prepared in Example II with an organolithium and a metal halide.

The bridged metallocene was prepared by dissolving a bridged compound synthesized in Example II in ether and the resulting solution was mixed with 2 mol equivalents of butyllithium (1.6M in hexane). After the evolution of gas had been completed, 1 mol equivalent of zirconium tetrachloride was added and the mixtures was stirred for 30-60 min.

After the solvent was removed, the residue was extracted with a small amount of methylene chloride and the suspension was filtered over sodium sulfate in order to remove lithium chloride formed. After concentrating the solution by evaporation, extraction took place with hexane followed by crystallization at −30° C.

In the case of the bisfluorenyl complex compounds which have a low solubility, purification was accomplished by extracting the crude product with ether using a Soxhlet apparatus. The starting materials and other impurities were removed as a result.

The reaction proceeded virtually quantitatively. In the solid state, all the compounds were stable with respect to oxygen and moisture. The bridged metallocenes thus prepared were 1-cyclopentadienyl-9-fluorenyldimethylsilanezirconium dichloride, 1-cyclopentadienyl-9(2,7-ditbutylfluorenyl)dimethylsilanezirconium dichloride, (1-cyclopentadienyl)- (2,7-di-t-butylftuorenyldimethylsilanezirconium dichloride, 9- (2,7-di-t-butylfluorenyl)-9-fluorenyldimethylsilanezirconium dichloride, 9- ( 2,7-di-t-butylfluorenyl)-9'- fluorenyldiphenylsilanezirconium dichloride, (1-cyclopentadienyl)(9-fluorenyl)dimethylgermanezirconium dichloride.

Example IV

This example illustrates the preparation of a silica-bonded, bridged ligand.

Fluorene (20 g; 120 mmol) was dissolved in 200 mL of ether and slowly mixed with 76 mL of butyllithium (1.6M in hexane). After the evolution of gas had been completed, the mixture was stirred for 1 hour at room temperature and then the solvent was removed. The solid fluorenyllithium (see Table II, footnote b) was added in portions to a solution of 36 g (40 mL, 241 mmol) of methyltrichlorosilane in 700 mL of pentane. After completion of the addition, the mixture was stirred for a further period of 1 hour at room temperature and the reaction mixture was then filtered over sodium sulfate. The solution was concentrated by evaporation to 30% of its volume and crystallized at −30° C. The product, 9-fluorenylmethyldichlorosilane, was generated in the form of a white crystalline powder (yield: 95%).

9-Fluorenylmethyldichlorosilane (5 g; 7.9 mmol) was then dissolved in 100 ml of ether and the resulting solution was mixed with 1.6 g (18 mmol) of cyclopentadienyl sodium. After 4 hours of stirring at room temperature, the reaction mixture was filtered over sodium sulfate and the solvent was removed. A bright yellow crude product (1-cyclopentadienyl-9-fluorenylmethylchlorosilane) was obtained which contained 10% bis-fluorenylmethylchlorosilane.

The crude product (5 g) obtained above was dissolved in 100 ml of toluene and the resulting solution was mixed with 5 g of silica gel (Merck No. 7713) and 10 ml of pyridine. The mixture was held for 34 hours at 80° C. and then cooled to room temperature. The supernatant solution was decanted, the resulting product (silica-O-1-cyclopentadienyl-9-fluorenylmethylsilane) was washed several times with ether and then dried.

Example V

This example illustrates the preparation of a bridged metallocene chemically bonded to an inorganic support material.

The silica-O-1-cyclopentadienyl-9-fluorenylmethylsilane prepared in Example IV was suspended or slurtied in 100 ml of ether and mixed with 2 mole equivalents (20 ml) of butyllithium (1.6M in hexane) per silane. The reaction mixture was shaken for 24 hours at room temperature followed by washing several times with ether (100 ml). After the mixture was again suspended in 100 ml of ether, 5 g (1 mol equivalent) of zirconium tetrachloride per silane was added and the mixture was shaken for another 24 hours.

The reaction mixture was washed with ether as above and the suspension was filtered over sodium sulfate. A metallocene chemically bonded to silica, i.e., silica-O-1-cyclopentadienyl-9-fluorenylmethylsilane zirconium dichloride was obtained.

Example VI

This example illustrates the use of the bridged metallocene prepared in Example V as catalyst for olefin polymerization.

Ethylene polymerization was conducted for one hour at 90° C. in a 3.8 liter stirred, stainless steel reactor in the presence of isobutane diluent, hydrogen as a molecular weight: control agent and methylaluminoxane as the cocatalyst. First the metallocene catalyst was weighed in a dry box and slurried in n-hexane to which a solution of methylaluminoxane has been added. One milliliter of the toluene methylaluminoxane solution was used. It was purchased from Schering at a concentration of 1.1M. The charge order was metallocene/methylaluminoxane slurry and then 2 liters of isobutane. After heating these materials to 90° C., 45 psi hydrogen pressure drop on a 300 cc cylinder, and then ethylene was introduced so that the total reactor pressure was maintained at 435 psig for the entire hour. Ethylene was supplied on demand from a pressured reservoir as required during each run. Polymerization was terminated by venting ethylene and diluent. The polymer was recovered, dried and weighed to determine yields. Catalyst productivity is calculated by dividing polymer weight in grams by the weight of metallocene used in grams, or by the weight of metallocene plus methylaluminoxane in grams and is conveniently expressed as g polymer per g desired catalyst component per hour (g/g-hr).

The polymerization results polymer characteristics are shown in Table III below.

TABLE III

| Run No. | Catalyst g | Yield g | Productivity (g/g-h) based on Metallocene | Productivity (g/g-h) based on Metallocene and MAO[a] |
|---|---|---|---|---|
| 1[b] | 0.5 | 0.4 | 8 | 3.5 |
| 2[c] | 0.5 | 1.5 | 30 | 13.2 |

[a]MAO, methylaluminoxane.
[b]The catalyst used in this run was silica-0-1-cyclopentadienyl-9-fluorenylmethyl silane zirconium dichloride.
[c]The catalyst used in this run was silica-0-1-cyclopentadienyl-9-fluorenylmethyl silane zirconium dichloride. This catalyst differed from run 1 in that the silica in run 2 was undried.

The results demonstrate that the supported, bridged metallocenes are useful as olefin polymerization catalyst.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A composition comprising a bridged metallocene having the formula of

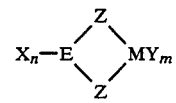

wherein each Z is the same or different hydrocarbyl radical selected from the group consisting of cyclopentadienyl, indenyl, tetrahydoindenyl, fluorenyl, and mixtures thereof; n is an integer of 1 or 2; one X is OQ; if n=2, the other X is selected from the group consisting of hydrogen fluorine, chlorine, bromine, iodine, R, OR, NR$_2$, PR$_2$, OQ, and mixtures thereof wherein the R is a C$_1$–C$_{20}$ hydrocarbyl radical and Q is an inorganic moiety selected from the group consisting of silica, alumina, clay, phosphated alumina, and mixtures thereof; each Y is the same or different and is selected from the group consisting of an alkyl group, hydrogen, fluorine, chlorine, bromine, iodine, and mixtures thereof; E is selected from the group consisting of C, Sn, Si, Ge, B, Al, N, P, and mixtures thereof; M is a metal selected from the group consisting of Ti, Zr, Hf, Sc, Y, V, La, and mixtures thereof; and m is a number sufficient to fill out the remaining valences of metal M.

2. A composition according to claim 1 wherein E is Si.

3. A composition according to claim 1 wherein X is selected from the group consisting of chlorine, methyl group, -O-alumina, -O-silica, and mixtures thereof.

4. A composition according to claim 1 wherein the other X is chlorine.

5. A composition according to claim 1 wherein Y is selected from the group consisting of chlorine, methyl group, and mixtures thereof.

6. A composition according to claim 5 wherein Y is chlorine.

7. A composition according to claim 1 wherein Z is selected from the group consisting of cyclopentadienyl radical, fluorenyl radical, and mixtures thereof.

8. A composition according to claim 1 further comprising an organoaluminoxane.

9. A composition according to claim 8 wherein said organoaluminoxane is methylaluminoxane.

10. A composition according to claim 1 wherein OQ is selected from the group consisting of -O-alumina, -O-silica, and mixtures thereof.

11. A composition according to claim 10 wherein OQ is -O-silica.

12. A composition according to claim 1 wherein M is selected from the group consisting of Ti, Zr, Hf, and mixtures thereof.

13. A composition according to claim 12 wherein M is Zr.

14. A composition according to claim 1 wherein said metallocene is selected from the group consisting of silica-O-1-cyclopentadienyl-1-cyclopentadienylmethylsilane zirconium dichloride, silica-O-bis(9-fluorenyl)phenylsilane zirconium dichloride, silica-O-1-cyclopentadienyl-9-fluorenylmethylsilane hafnium dichloride, silica-O-bis(9-fluorenyl)phenylsilane hafnium dichloride, silica-O-1-cyclopentadienyl-9-fluorenylmethylsilane vanadium dichloride, silica-O-bis(9-fluorenyl)phenylsilane vanadium dichloride, silica-O-1-cyclopentadienyl-9-fluorenylmethylsilane titanium dichloride, silica-O-bis(2,8-difluoro-9-fluorenyl)methylsilane zirconium dichloride, silica-O-1-cyclopentadienyl-9-fluorenylmethylchlorosilane zirconium dichloride, silica-O-bis(9-fluorenyl)phenylchlorosilane zirconiumdichloride, silica-O-1-cyclopentadienyl-9-fluorenylmethylchlorosilane hafnium dichloride, silica-O-bis(9-fluorenyl)phenylchlorosilane hafnium dichloride, silica-O-1-cyclopentadienyl -9-fluorenylmethylchlorosilane vanadium dichloride, silica-O-bis(9-fluorenyl)phenylchlorosilane vanadium dichloride, silica-O-1-cyclopentadienyl-9-flurorenylmethylchlorosilane titanium dichloride, silica-O-bis(9-fluorenyl)phenylchlorosilane titanium dichloride, silica-O-bis(2,8-difluoro-9-fluorenyl)methylchlorosilanezirconium dichloride, silica-O-1-cyclopentadienyl-9-fluorenylmethylsilane zirconium dichloride, alumina-O-1-cyclopentadienyl-9-fluorenylmethylsilane zirconium dichloride, bentonite-O-1-cyclopentadienyl-9-fluorenylmethylsilane zirconium dichloride, and mixtures thereof.

15. A composition according to claim 14 wherein said metallocene is silica-O-1-cyclopentadienyl-9-fluorenylmethylsilane zirconium dichloride.

16. A process comprising contacting a bridged ligand having the formula of ZH-EX$_n$-ZH with an inorganic material QOH to form a bridged ligand chemically bonded to inorganic moiety Q wherein each Z is the same or different hydrocarbyl radical selected from the group consisting of cyclopentadienyl, indenyl, tetrahydroindenyl, fluorenyl, and mixtures thereof; each X is the same or different and is selected from the group consisting of hydrogen, fluorine, chlorine, bromine, iodine, R, OR, NR$_2$, PR$_2$, OQ, and mixtures thereof wherein at least one X is a halogen R is a C$_1$–C$_{20}$ hydrocarbyl radical and Q is an inorganic moiety selected from the group consisting of silica, alumina, clay, phosphated alumina, and mixtures thereof; each E is selected from the group consisting of C, Sn, Si, Ge, B, Al, N, P, and O; and n is an integer of from 1 to 2.

17. A process according to claim 16 wherein E is Si.

18. A process according to claim 16 wherein X is selected from the group consisting of chlorine, methyl group, phenyl group, -O-alumina, -O-silica, and mixtures thereof.

19. A process according to claim 16 wherein said halogen is chlorine.

20. A process according to claim 16 wherein Z is selected from the group consisting of cyclopentadienyl radical, fluorenyl radical, and mixtures thereof.

21. A process according to claim 16 wherein OQ is selected from the group consisting of -O-silica, -O-alumina, and mixtures thereof.

22. A process according to claim 21 wherein OQ is -O-silica.

23. A process according to claim 16 wherein said bridged ligand is selected from the group consisting of 1-cyclopentadienyl-9-fluorenylmethylchlorosane, 1-cyclopentadienyl-1-cyclopentadienylmethylchlorosilane, and mixtures thereof.

24. A process according to claim 16 wherein said bridged ligand chemically bonded to inorganic moiety is silica-O-1-cyclopentadienyl-9-fluorenylmethylsilane.

25. A process for preparing a bridged metallocene comprising: (1) contacting a hydrocarbon having at least two acidic, replaceable hydrogens and having the formula of ZH$_2$ with an organolithium and an organohalocompound to prepare a ligand precursor having the formula of HZ-EX$_{n+1}$ wherein at least two X's are halogens; (2) contacting said ligand precursor with an organo alkali metal compound having the formula of HZMa to form a bridged ligand having the formula of ZH-EX$_n$-ZH wherein at least one X is a halogen; (3) contacting said bridged ligand with an inorganic material QOH to form a bridged ligand chemically bonded to inorganic moiety Q; (4) contacting said bridged ligand chemically bonded to inorganic moiety with an organolithium and a metal halide having the formula of MY$_m$ to prepare said bridged metallocene; wherein each Z is the same or different hydrocarbyl radical selected from the group consisting of cyclopentadienyl, indenyl, tetrahydroindenyl, fluorenyl, and mixtures thereof; each X is the same or different and is selected from the group consisting of hydrogen, fluorine, chlorine, bromine, iodine, R, OR, NR$_2$, PR$_2$, OQ, and mixtures thereof wherein the R is a C$_1$–C$_{20}$ hydrocarbyl radical and Q is an inorganic moiety selected from the group consisting of silica, alumina, clay, phosphated alumina, and mixtures thereof; each Y is the same or different and is selected from the group consisting of an alkyl group, hydrogen, fluorine, chlorine, bromine, iodine, and mixtures thereof; each E is selected from the group consisting of C, Sn, Si, Ge, B, Al, N, P, and mixtures thereof; M is a metal selected from the group consisting of Ti, Zr, Hf, Sc, Y, V, La, and mixtures thereof; m is a number sufficient to fill out the remaining valences of metal M; Ma is an alkali metal; and n is 1 or 2.

26. A process according to claim 25 wherein said halogen is chlorine.

27. A process according to claim 25 wherein Z is selected from the group consisting of cyclopentadienyl radical, fluorenyl radical, and mixtures thereof.

28. A process according to claim 25 wherein OQ is selected from the group consisting of -O-silica, -O-alumina, and mixtures thereof.

29. A process according to claim 28 wherein OQ is -O-silica.

30. A process according to claim 25 wherein M is selected from the group consisting of Ti, Zr, Hf, and mixtures thereof.

31. A process according to claim 30 wherein M is Zr.

32. A process according to claim 25 wherein Y is chlorine.

33. A process according to claim 25 wherein said metallocene is selected from the group consisting of silica-O-1-cyclopentadienyl-1-cyclopentadienylmethylsilane zirconium dichloride, silica-O-bis(9-fluorenyl)phenylsilane zirconium dichloride, silica-O-1-cyclopentadienyl-9-fluroenylmethylsilane hafnium dichloride, silica-O-bis(9-fluorenyl)phenylsilane hafnium dichloride, silica-O-1-cyclopentadienyl-9-fluorenylmethylsilane vanadium dichloride, silica-O-bis(9-fluorenyl)phenylsilane vanadium dichloride, silica-O-1-cyclopentadienyl-9-fluorenylmethylsilane titanium dichloride, silica-O-bis(9-fluorenyl)phenylsilane titanium dichloride, silica-O-bis(2,8-difluoro-9-fluorenyl)methylsilane zirconium dichloride, silica-O-1-cyclopentadienyl-9-fluorenylmethylchlorosilane zirconium dichloride, silica-O-bis(9-fluorenyl)phenylchlorosilane zirconium dichloride, silica-O-1-cyclopentadienyl-9-fluorenylmethylchlorosilane hafnium dichloride, silica-O-bis(9-fluorenyl)phenylchlorosilane hafnium dichloride, silica-O-1-cyclopentadienyl-9-fluorenylmethylchlorosilane vanadium dichloride, silica-O-bis(9-fluorenyl)phenylchlorosilane vanadium dichloride, silica-O-1-cyclopentadienyl-9-fluorenylmethylchlorosilane titanium dichloride, silica-O-bis(9-fluorenyl)phenylchlorosilane titanium dichloride, silica-O-bis(2,8-difluoro-9-fluorenyl)methylchlorosilane zirconium dichloride, silica-O-1-cyclopentadienyl-9-fluorenylmethylsilane zirconium dichloride, alumina-O-1-cyclopentadienyl-9-fluorenylmethylsilane zirconium dichloride, bentonite-O-1-cyclopentadienyl-9-fluorenylmethylsilane zirconium dichloride, and mixtures thereof.

34. A process according to claim 33 wherein said metallocene is silica-O-1-cyclopentadienyl-9-fluorenylmethylsilane zirconium dichloride.

35. A process according to claim 25 wherein said organohalocompound is an organochlorosilane.

36. A process for preparing a bridged metallocene having the formula of

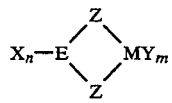

comprising: (1) contacting a hydrocarbon having at least two acidic, replaceable hydrogens and having the formula of $ZH_2$ with an organolithium and an organohalocompound to prepare a ligand precursor having the formula of $HZ\text{-}EX_{n+1}$ wherein at least two X's are halogens; (2) contacting said ligand precursor with an organo alkali metal compound having the formula of HZMa to form a bridged ligand having the formula of $ZH\text{-}EX_n\text{-}ZH$ wherein at least one X is a halogen; (3) contacting said bridged ligand with an organolithium and a metal halide having the formula of $MY_m$ to prepare said bridged metallocene; and (4) contacting said bridged metallocene with an organic material QOH to form a metallocene chemically bonded to Q; wherein each Z is the same or different hydrocarbyl radical selected from the group consisting of cyclopentadienyl, indenyl, tetrahydroindenyl, fluorenyl, and mixtures thereof; each X is the same or different and is selected from the group consisting of hydrogen, fluorine, chlorine, bromine iodine, R, OR, NR, PR, OQ, and mixtures thereof wherein the R is a $C_1$–$C_{20}$ hydrocarbyl radical and Q is an inorganic moiety selected from the group consisting of silica, alumina, clay phosphated alumina, and mixtures thereof; each Y is the same or different and is selected from the group consisting of an alkyl group, hydrogen, fluorine, chlorine, bromine, iodine, and mixtures thereof; each E is selected from the group consisting of Sn, Si, Ge, B, Al, N, P, and mixtures thereof; M is a metal selected from the group consisting of Ti, Zr, Hf, Sc, Y, V, La, and mixtures thereof; m is a number sufficient to fill out the valence of the metal M; Ma is an alkali metal; and n is 1 or 2.

37. A process comprising: (1) contacting a hydrocarbon selected from the group consisting of cyclopentadiene, fluorene, and mixtures thereof with butyllithium and an organosilane selected from the group consisting of methyltrichlorosilane, phenyltrichlorosilane, and mixtures thereof to prepare a ligand precursor; (2) contacting said ligand precursor with an organo alkali metal compound selected from the group consisting of cyclopentadienyllithium, cyclopentadienylsodium, fluorenyllithium, fluorenylsodium, and mixtures thereof to prepare a bridged ligand; (3) contacting said bridged ligand with silica to form a bridged ligand chemically bonded to silica; (4) contacting the bridged ligand chemically bonded to silica with zirconium chloride to form a metallocene.

38. A process for ethylene polymerization comprising contacting ethylene, under ethylene polymerization conditions, with silica-O-1-cyclopentadienyl-9-fluorenylmethylsilane zirconium dichloride.

39. A process for olefin polymerization comprising contacting an olefin under olefin polymerization conditions with a composition comprising a bridged metallocene having the formula of:

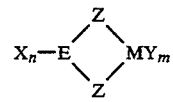

wherein each Z is the same or different hydrocarbyl radical selected from the group consisting of cyclopentadienyl, indenyl, tetrahydroindenyl, fluorenyl, and mixtures thereof; each X is the same or different and is selected from the group consisting of hydrogen, fluorine, chlorine, bromine, iodine, R, OR, $NR_2$, $PR_2$, OQ, and mixtures thereof wherein one X is OQ, R is a $C_1$–$C_{20}$ hydrocarbyl radical and Q is an inorganic moiety selected from the group consisting of silica, alumina, clay, phosphated alumina, and mixtures thereof; each Y is the same or different and is selected from the group consisting of an alkyl group, hydrogen, fluorine, chlorine, bromine, iodine, and mixtures thereof; each E is selected from the group consisting of Sn, Si, Ge, B, Al, N, P, and mixtures thereof; M is a metal selected from the group consisting of Ti, Zr, Hf, Sc, Y, V, and La; n is 1 or 2; and m is a number sufficient to fill out the remaining valences of the metal M.

40. A process according to claim 39 wherein said composition further comprises an activator selected from the group consisting of an organoaluminoxane, an organoaluminum, an organometallic compound of Groups IA, IIA, and IIIB of the Periodic Table of Elements, tris-perfluorophenyl borate, trityl tetra-perfluorophenyl borate, and mixtures thereof.

41. A process according to claim 40 wherein said organoaluminoxane is methylaluminoxane.

42. A process according to claim 39 wherein E is Si.

43. A process according to claim 39 wherein X is selected from the group consisting of chlorine, methyl radical, -O-alumina, -O-silica, and mixtures thereof.

44. A process according to claim 39 wherein the other X is chlorine.

45. A process according to claim 39 wherein Y is selected from the group consisting of chlorine, methyl group, and mixtures thereof.

46. A process according to claim 39 wherein Z is selected from the group consisting of cyclopentadienyl radical, fluorenyl radical, and mixtures thereof.

47. A process according to claim 39 wherein OQ is selected from the group consisting of -O-alumina, -O-silica, and mixtures thereof.

48. A process according to claim 39 wherein OQ is -O-silica.

49. A process according to claim 39 wherein M is selected from the group consisting of Ti, Zr, Hf, and mixtures thereof.

50. A process according to claim 39 wherein M is Zr.

51. A process according to claim 39 wherein Y is chlorine.

52. A process according to claim 39 wherein said metallocene is selected from the group consisting of silica-O-1-cyclopentadienyl-1-cyclopentadienylmethylsilane zirconium dichloride, silica-O-bis(9-fluorenyl)phenylsilane zirconium dichloride, silica-O-1-cyclopenadienyl-9-fluorenylmethylsilane hafnium dichloride, silica-O-bis(9-fluorenyl)phenylsilane hafnium dichloride, silica-O-1-cyclopentadienyl-9-fluorenylmethylsilane vandium dichloride, silica-O-bis(9-fluorenyl)phenylsilane vandium dichloride, silica-O-1-cyclopentadienyl-9-fluorenylmethylsilane titanium dichloride, silica-O-bis(9-fluorenyl)phenylsilane titanium dichloride, silica-O-bis(2,8-difluoro-9-fluorenyl)methylsilane zirconium dichloride, silica-O-1-cyclopentadienyl-9-fluorenylmethylchlorosilane zirconium dichloride, silica-O-bis(9-fluorenyl)phenylchlorosilane zirconium dichloride, silica-O-1-cyclopentadienyl-9-fluorenylmethylchlorosilane hafnium dichloride, silica-O-bis(9-fluorenyl)phenylchorosilane hafnium dichloride silica-O-1-cyclopentadienyl-9-fluorenylmethylchorosilane vanadium dichloride, silica-O-bis(9-fluorenyl)phenylchlorosilane vanadium dichloride, silica-O-1-cyclopentadienyl-9-fluorenylmethylchlorosilane titanium dichloride, silica-O-bis(9-fluorenyl)phenylchlorosilane titanium dichloride, silica-O-bis(2,8-difluoro-9-fluorenyl)methylchlorosilanezirconiumdichloride, silica-O-1-cyclopentadienyl-9-fluorenylmethylsilane zirconium dichloride, alumina-O-1-cyclopentadienyl-9-fluorenylmethylsilane zirconium dichloride, bentonite-O-1-cyclopentadienyl-9-fluorenylmethylsilane zirconium dichloride, and mixtures thereof.

53. A process according to claim 39 wherein said metallocene is silica-O-1-cyclopentadienyl-9-fluorenylmethylsilane zirconium dichloride.

54. A composition produced by the process comprising contacting an olefin under olefin polymerization conditions with a composition comprising a bridged metallocene having the formula of:

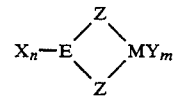

wherein each Z is the same or different hydrocarbyl radical selected from the group consisting of cyclopentadienyl, indenyl, tetrahydroindenyl, fluorenyl, and mixtures thereof; each X is the same or different and is selected from the group consisting of hydrogen, fluorine, chlorine, bromine, iodine, R, OR, $NR_2$, $PR_2$, OQ, and mixtures thereof wherein one X is OQ, R is a $C_1$–$C_{20}$ hydrocarbyl radical and Q is an inorganic moiety selected from the group consisting of silica, alumina, clay, phosphated alumina, and mixtures thereof; each Y is the same or different and is selected from the group consisting of an alkyl group, hydrogen, fluorine, chlorine, bromine, iodine, and mixtures thereof; each E is selected from the group consisting of Sn, Si, Ge, B, Al, N, P, and mixtures thereof; M is a metal selected from the group consisting of Ti, Zr, Hf, Sc, Y, V, and La; n is 1 or 2; and m is a number sufficient to fill out the remaining valences of metal M.

* * * * *